US008466248B2

(12) United States Patent  
Meyer et al.

(10) Patent No.: US 8,466,248 B2  
(45) Date of Patent: Jun. 18, 2013

(54) USE OF EMULSIFIER SYSTEMS CONTAINING ORGANOMODIFIED SILOXANE BLOCK COPOLYMERS FOR THE PREPARATION OF COSMETIC OR PHARMACEUTICAL COMPOSITIONS

(75) Inventors: Juergen Meyer, Essen (DE); Frank Unger, Duisburg (DE); Michael Ferenz, Essen (DE); Sascha Herrwerth, Essen (DE); Christian Hartung, Essen (DE); Andrea Lohse, Bottrop (DE)

(73) Assignee: Evonik Goldschmidt GmbH, Essen (DE)

( * ) Notice: Subject to any disclaimer, the term of this patent is extended or adjusted under 35 U.S.C. 154(b) by 209 days.

(21) Appl. No.: 12/991,255

(22) PCT Filed: Apr. 15, 2009

(86) PCT No.: PCT/EP2009/054426  
§ 371 (c)(1),  
(2), (4) Date: Nov. 5, 2010

(87) PCT Pub. No.: WO2009/138306  
PCT Pub. Date: Nov. 19, 2009

(65) Prior Publication Data  
US 2011/0091399 A1 Apr. 21, 2011

(30) Foreign Application Priority Data  
May 15, 2008 (DE) .......................... 10 2008 001 788

(51) Int. Cl.  
*C08G 77/12* (2006.01)

(52) U.S. Cl.  
USPC ............................ 528/25; 528/31

(58) Field of Classification Search  
USPC .................................... 528/31, 25  
See application file for complete search history.

(56) References Cited

U.S. PATENT DOCUMENTS

| 4,853,474 | A * | 8/1989 | Bahr et al. ............... 556/445 |
|---|---|---|---|
| 2005/0136269 | A1 | 6/2005 | Doehler et al. |
| 2005/0287300 | A1 | 12/2005 | Herrwerth et al. |
| 2006/0041097 | A1 | 2/2006 | Herrwerth et al. |
| 2006/0155089 | A1 | 7/2006 | Ferenz et al. |
| 2006/0155090 | A1 | 7/2006 | Ferenz |
| 2006/0188455 | A1 | 8/2006 | Ferenz et al. |
| 2006/0188456 | A1 | 8/2006 | Ferenz et al. |
| 2007/0100153 | A1 | 5/2007 | Brueckner et al. |
| 2007/0184006 | A1 | 8/2007 | Ferenz et al. |
| 2007/0299231 | A1 | 12/2007 | Doehler et al. |
| 2008/0027202 | A1 | 1/2008 | Ferenz et al. |
| 2008/0216708 | A1 | 9/2008 | Herrwerth et al. |
| 2008/0305065 | A1 | 12/2008 | Ferenz et al. |
| 2009/0062459 | A1 | 3/2009 | Thum et al. |
| 2010/0034765 | A1 | 2/2010 | Herrwerth et al. |
| 2010/0056649 | A1 | 3/2010 | Henning et al. |
| 2010/0056818 | A1 | 3/2010 | Ferenz et al. |
| 2010/0081763 | A1 | 4/2010 | Meyer et al. |

FOREIGN PATENT DOCUMENTS

| DE | 1165574 | 8/1960 |
|---|---|---|
| DE | 3740186 A1 | 1/1989 |
| DE | 3938140 A1 | 8/1991 |
| DE | 4009347 A1 | 9/1991 |
| DE | 4238081 A1 | 7/1993 |
| DE | 4204321 A1 | 8/1993 |
| DE | 4229707 A1 | 3/1994 |
| DE | 4229737 A1 | 3/1994 |
| DE | 4309372 A1 | 9/1994 |
| DE | 4324219 A1 | 1/1995 |
| DE | 19855934 A1 | 6/2000 |
| DE | 10 2005 001 040 A1 | 7/2006 |
| DE | 10 2005 001 041 A1 | 7/2006 |
| EP | 0 298 402 A2 | 1/1989 |
| EP | 0666732 B1 | 1/1997 |
| EP | 1 125 574 A2 | 8/2001 |
| EP | 1 679 335 A2 | 7/2006 |
| EP | 1 892 327 A1 | 2/2008 |
| WO | WO 2009/138305 A1 | 11/2009 |
| WO | WO 2009/138306 A1 | 11/2009 |

OTHER PUBLICATIONS

"Kosmetische Färbemitter" [Cosmetic Colouring Agents] of the Farbstoffkommission der Deutschen Forschungsgemeinschaft [Colorant Commission of the German Research Association], Verlag Chemie, Weinheim, 1984, pp. 81-106.  
Finkel, P., et al., "Formulierung Kometischer Sonnenschutzmittel", 1996, SÖFW-journal, vol. 122, p. 543.  
U.S.Appl. No. 12/761,750 entitled "Emulsifier Including Glycerin-Modified Organopolysiloxanes", filed Apr. 16, 2010, first named inventor: Karin Czech.  
International Search Report dated Oct. 1, 2009.  
Abstract of European Patent Publication No. EP 1679335, dated Jul. 12, 2006.

* cited by examiner

*Primary Examiner* — Kuo-Liang Peng  
(74) *Attorney, Agent, or Firm* — Scully, Scott, Murphy & Presser, P.C.

(57) ABSTRACT

The invention relates to emulsifier systems comprising organomodified siloxane block copolymers, their use, in particular the preparation of cosmetic, dermatological or pharmaceutical formulations, and of care and cleaning compositions, and also the products themselves prepared with the help of emulsifier systems.

18 Claims, No Drawings

USE OF EMULSIFIER SYSTEMS CONTAINING ORGANOMODIFIED SILOXANE BLOCK COPOLYMERS FOR THE PREPARATION OF COSMETIC OR PHARMACEUTICAL COMPOSITIONS

Use of emulsifier systems containing organomodified siloxane block copolymers for the preparation of cosmetic or pharmaceutical compositions.

FIELD OF THE INVENTION

The invention relates to emulsifier systems which comprise organomodified siloxane block copolymers, and to cosmetic, dermatological or pharmaceutical formulations which comprise these emulsifier systems.

PRIOR ART

Organomodified siloxanes are used in a very wide variety of applications. Their properties can be adjusted, inter alia, through the type of modification, and also by the density of modification.

Thus, for example, it is possible to use allyl polyethers to attach organophilic or nonionic hydrophilic groups to a siloxane backbone. Compounds of this type are used, for example, as polyurethane foam stabilizers, as defoamers in fuels or as additives in paints and coatings.

Thus, for example, DE 102005001041 describes functionalized polyorganosiloxanes and their use as fuel defoamer. The allyl polyethers in the siloxanes described here can, if appropriate, be replaced by altering the synthesis through hydrocarbon radicals.

In general, siloxanes can be linked through reaction with, for example, $\alpha$-olefins having hydrophobic groups. The silicone waxes obtained in this way serve, for example, as additive in personal care applications.

It is apparent in many fields of application that the effect of the siloxane is decisively dependent on the compatibility with the formulation in question.

Suitable cosmetic emulsifiers are, for example, siloxanes which carry polyethers besides aliphatic groups based on $\alpha$-olefins. A typical example here is the commercial product ABIL EM 90 from Evonik Goldschmidt GmbH (Germany), which stands out in particular due to excellent stabilization of water-in-oil (W/O) emulsions.

Siloxane-based emulsifiers for oil-in-water (O/W) emulsions must have a relatively hydrophilic character, for which reason these products are generally pure polyethersiloxanes.

EP 1125574 describes the use of relatively hydrophobic polyethersiloxanes as O/W emulsifiers in which the polyether groups are located on the siloxane backbone in the $\alpha$-$\omega$-position or terminal position. These structures stand out in particular due to a velvety silky skin feel, which they are able to incorporate into cosmetic emulsions.

A disadvantage of using these structures is the often inadequate emulsifiability.

EP0298402 describes the use of organopolysiloxane-polyoxyalkylenes as emulsifier in water-in-oil emulsions and constitutes the known closest prior art. The organopolysiloxane-polyoxyalkylenes are distinguished in that two organopolysiloxane-polyoxyalkylene molecules are joined together via a non-hydrolysable crosslinker which is as short as possible. During the preparation of these polymers, the molar ratio of vinylic crosslinker to organopolysiloxane-polyoxyalkylene molecules to be linked is very large. This leads to unbeneficial by-products. For this reason too, the emulsifier systems described in EP0298402 are, inter alia, only suitable for cosmetic applications with limitations.

It was therefore an object of the present invention to develop new types of organomodified siloxanes which can be used as high-performance emulsifiers both in O/W and also in W/O emulsions and, especially in O/W emulsions, are able to combine a velvety-silky skin feel with excellent emulsifying properties.

Moreover, these siloxanes should preferably be easy to process (liquid at room temperature) and can be combined with conventional siloxanes in formulations.

DESCRIPTION OF THE INVENTION

Surprisingly, it has been found that organomodified siloxane block copolymers prepared by a process described in Claim 1 are high-performance emulsifiers, particularly for cosmetic, dermatological or pharmaceutical formulations, which are able to achieve this object.

The invention therefore provides emulsifier systems which comprise organomodified siloxane block copolymers prepared by a process described in Claim 1.

A particular advantage of the emulsifier systems according to the invention is their excellent emulsifying and stabilizing properties.

It is a further advantage that they make it possible to incorporate a velvety-silky skin feel into cosmetic formulations. This is important insofar as consumers are considering it increasingly important that cosmetic formulations can not only be spread easily and absorb well into the skin, but that, following absorption, a smooth, soft, velvety impression remains.

A further advantage of the emulsifier systems according to the invention is that the properties of laterally modified siloxanes and of $\alpha,\omega$-modified siloxanes are combined therein, and thus the degree of modification in the sense of a larger number of substitution options is higher.

The emulsifier systems of the invention are described below by way of example without any intention to limit the invention to these exemplary embodiments. Where ranges, general formulae or compound classes are given below, then these are intended to include not only the corresponding ranges or groups of compounds explicitly mentioned, but also all part ranges and subgroups of compounds which can be obtained by removing individual values (ranges) or compounds. Where documents are cited within the context of the present description, then their contents should in their entirety belong to the disclosure content of the present invention. If, within the context of the present invention, compounds such as, for example, organomodified polysiloxanes, are described which may have different units several times, then these can occur in these compounds in random distribution (random oligomer) or arranged (block oligomer). Data relating to the number of units in such compounds is to be understood as an average value, averaged over all of the corresponding compounds. Within the context of this invention, an emulsifier system is to be understood as meaning an emulsifier which comprises at least one substance of the general formula (I) and optionally at least one coemulsifier.

The invention therefore provides emulsifier systems which comprise organomodified siloxane block copolymers which have been prepared by A) addition reaction of organopolysiloxanes of the general formula I

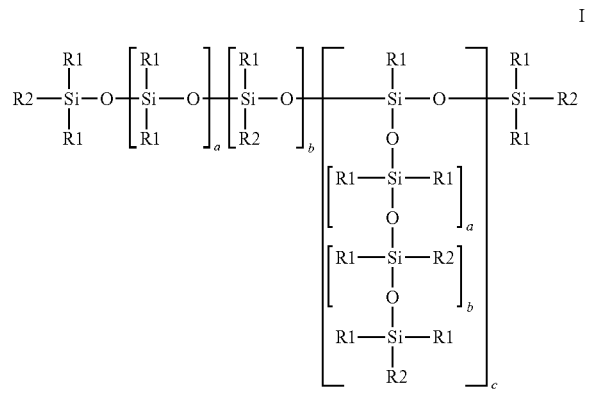

in which
R$^1$ are identical or different, branched or unbranched, aliphatic or aromatic hydrocarbon radicals having 1 to 20 carbon atoms,
R$^2$ is R$^1$ or H, with the proviso that at least three radicals R$^2$ are H,
a is 5 to 500, preferably 10 to 250, in particular 15 to 75,
b is 1 to 50, preferably 1 to 20, in particular 3 to 15,
c is 0 to 5, preferably 0 to 1, in particular 0,
onto siloxanes of the general formula II containing double bonds

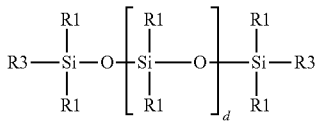

where
d is 10 to 1000, preferably 101 to 750, in particular 201 to 500 and
R$^3$, independently of one another, are identical or different hydrocarbon radicals having 2 to 12, preferably 2 to 8, in particular 2 carbon atoms and containing at least one double bond,
in the presence of platinum or rhodium catalysts, with the proviso that the organopolysiloxanes of the general formula I are present in at least 6-fold molar excess, based on the siloxane of the general formula II containing double bonds, to give a reaction product having Si—H groups and with further reaction of the reaction product in at least one of the stages
B) transition-metal-catalysed partial or complete addition of the SiH groups onto alkenyl and/or alkynyl compounds, preferably onto double-bond-containing polyethers and α-olefins, in particular onto allyl polyethers,
or
C) partial or complete reaction of the Si—H groups remaining after the above reaction(s) in the presence of a catalyst with at least one alcohol, from the group of linear or branched, saturated, mono- or polyunsaturated, aromatic, aliphatic-aromatic, optionally halogen-atom-containing monoalcohols, polyether monoalcohols, polyester monoalcohols, amino alcohols.

The radicals R$^1$ are preferably identical or different aliphatic or aromatic hydrocarbon radicals having 1 to 20 carbon atoms, further preferably identical or different unbranched, aliphatic or aromatic hydrocarbon radicals having 1 to 9 carbon atoms and particularly preferably methyl, ethyl or phenyl.

The proviso that the SiH-group-carrying organopolysiloxane of the general formula I is present in at least 6-fold molar excess, based on the double bond-containing siloxane of the general formula II, prevents the formation of a network and the formation of highly viscous products resulting. As a rule, the organosiloxanes prepared by one of the two aforementioned processes have viscosities up to 10 000 mPas. A certain fraction of the organosiloxane may be present in the product in the form of a comb-like modified siloxane.

On account of the selected reaction conditions, the double-bond-containing siloxane and the Si-functional siloxane form, in the first stage, a siloxane of the following idealized "H structure" shown in formula III (c=0, R$^1$=Me, R$^2$=R=Me or H):

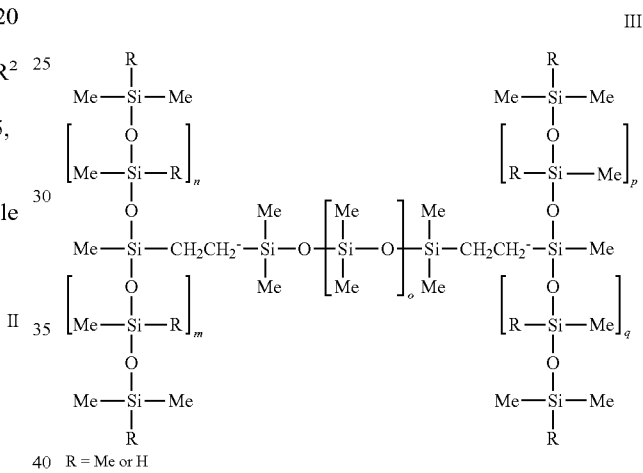

where m, n, o, p and q are positive integers.

This siloxane backbone is retained during subsequent reaction stages. The synthesis of the siloxane polymers can take place with or without solvents. Foaming which may possibly arise can be suppressed through the use of solvents. Suitable solvents are, for example, toluene and cyclohexane.

Effective catalysts which can be used for the first step, the hydrosilylation of the double-bond-containing siloxane A), are Pt- and Rh-containing complexes which are known to the person skilled in the art as hydrosilylation-active catalysts, for example: $H_2PtCl_6$, $Pt[(CH_2=CH-SiMe_2)_2O]_n$ or $Rh(CO)(C_5H_7O_2)$.

For the addition reaction of the alcohol in process step C) onto the resulting SiH-containing siloxane it is possible to use, for example, Lewis acids, preferably boron-containing Lewis acids. Boron-containing compounds of the catalytic system which may be used are fluorinated and/or nonfluorinated organoboron compounds, in particular those selected from:
$(C_5F_4)(C_6F_5)_2B$; $(C_5F_4)_3B$; $(C_6F_5)BF_2$; $BF(C_6F_5)_2$; $B(C_6F_5)_3$; $BCl_2(C_6F_5)$; $BCl(C_6F_6)_2$; $B(C_6H_5)(C_6F_5)_2$; $B(C_6H_5)_2(C_6F_5)$; $[C_6H_4(m-CF_3)]_3B$; $[C_6H_4(p-OCF_3)]_3B$; $(C_6F_5)B(OH)_2$; $(C_6F_5)_2BOH$; $(C_6F_5)_2BH$; $(C_6F_5)BH_2$; $(C_7H_{11})B(C_6F_5)_2$; $(C_8H_{14}B)(C_6F_5)$; $(C_6F_5)_2B(OC_2H_5)$; $(C_6F_5)_2B-CH_2CH_2Si(CH_3)_3$;

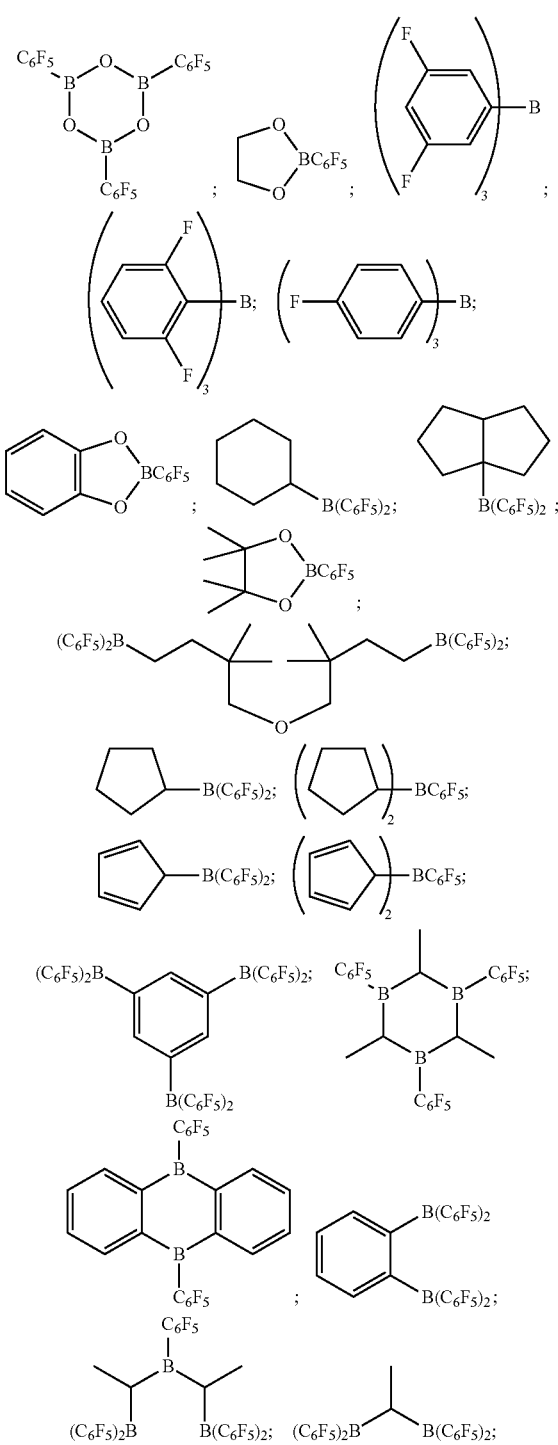

particularly preferably tris(pentafluorophenyl)borane [CAS No. 1109-15-5], and mixtures of the above catalysts.

When using these boron-containing catalysts, it is furthermore possible to use synergistically effective compounds. These include salts or complexes, with cations selected from the group of the salts of elements of the 4th, 6th, 7th and 8th subgroup and also of the 4th main group. Anions of the synergistically active compounds of the catalytic system which may be used are preferably alkoxylates, acid anions, in particular carboxylates, sulphates, nitrates or phosphates, halides, in particular chlorides, oxides or complex ligands, in particular acetyl acetonate or carbonyls.

In addition, DE10312634.1 describes a process for the preparation of organically modified polyorganosiloxanes using a catalytic mixture comprising at least one carboxylic acid and at least one salt of a carboxylic acid by linking hydrogen siloxanes with alcohols. These catalysts can also be used in process step C).

Suitable alcohols are, for example, linear or branched, saturated, mono- or polyunsaturated, aromatic, aliphatic-aromatic monoalcohols or polyalcohols, polyether monoalcohols, polyether polyalcohols, polyester monoalcohols, polyester polyalcohols, amino alcohols, in particular N-alkyl-, arylamino-EO—, —PO-alcohols (EO stands for the polyethylene oxide radical, PO for the polypropylene oxide radical), N-alkyl- or arylamino alcohols, and mixtures thereof. Polyether monoalcohols are particularly suitable.

Effective catalysts which can be used for the transition-metal-catalysed addition of the SiH groups of the siloxane prepared in the first step onto CC multiple bonds in process step B) are the known hydrosilylation catalysts, for example: $H_2PtCl_6$, $Pt[(CH_2=CH-SiMe_2)_2O]_n$ or $Rh(CO)(C_5H_7O_2)$.

Suitable alkenyl/alkynyl compounds are, for example, polyethers with multiple bonds, for example butanediol alkoxylates or allyl-functional polyethers, olefins, ethene, ethyne, propene, 1-butene, 1-hexene, 1-dodecene, 1-hexadecene, allyl alcohol, hex-5-en-1-ol, styrene, eugenol, allyl phenol, methyl undecylenate. Of particular suitability are polyethers with double bonds, in particular allyl-functional polyethers.

The emulsifier systems according to the invention are preferably used as oil-in-water emulsifiers, water-in-oil emulsifiers or water-in-silicone emulsifiers or dispersion auxiliaries. The present invention therefore also provides dispersion or emulsions comprising at least one of the emulsifier systems according to the invention.

The emulsifier system is preferably also used for the preparation of O/W impregnation emulsions for textiles. The textiles are preferably wet wipes, particularly preferably cosmetic wet wipes.

Based on the total mass, the emulsions and dispersions according to the invention comprise more mass percent of oil component than the sum of the mass percents of emulsifier, surfactant and optionally coemulsifier.

The oil-in-water emulsions, water-in-oil emulsions and water-in-silicone emulsions and dispersions obtained with the help of the emulsifier systems according to the invention, and also O/W impregnation emulsions for textiles are likewise provided by the invention. The textiles impregnated with O/W impregnation emulsions according to the invention are likewise provided by the invention. These are distinguished by good cleaning power and a pleasantly velvety-smooth skin feel.

The invention further provides the use of the emulsifier systems according to the invention for the preparation of cosmetic, dermatological or pharmaceutical formulations. The invention likewise provides the use of the emulsions and dispersions according to the invention for the preparation of cosmetic, dermatological or pharmaceutical formulations.

The cosmetic, dermatological or pharmaceutical formulation comprising at least one emulsifier system according to the invention or at least one emulsion or dispersion according to the invention is likewise provided by the invention.

The invention further provides the use of the emulsifier systems or of emulsion or dispersion according to the invention for the preparation of care and cleaning compositions optionally comprising dispersed solids for domestic use or industry, in particular for hard surfaces, leather or textiles. The care and cleaning compositions for domestic use or industry and the care and cleaning compositions for hard surfaces, leather or textiles are likewise provided by the invention.

The cosmetic, dermatological or pharmaceutical formulations and also the care and cleaning compositions can comprise, for example, at least one additional component selected from the group of emollients,
emulsifiers and surfactants,
thickeners/viscosity regulators/stabilizers,
UV photoprotective filters,
antioxidants,
hydrotropes (or polyols),
solids and fillers,
film-formers,
pearlescent additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Emollients which can be used are all cosmetic oils, in particular mono- or diesters of linear and/or branched mono- and/or dicarboxylic acids having 2 to 44 carbon atoms with linear and/or branched saturated or unsaturated alcohols having 1 to 22 carbon atoms. It is likewise possible to use the esterification products of aliphatic, difunctional alcohols having 2 to 36 carbon atoms with monofunctional aliphatic carboxylic acids having 1 to 22 carbon atoms. Also suitable are long-chain aryl acid esters, such as, for example, esters of benzoic acid, e.g. benzoic acid esters of linear or branched, saturated or unsaturated alcohols having 1 to 22 carbon atoms, or else isostearyl benzoate or octyldodecyl benzoate. Further monoesters suitable as emollients and oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and esters which are obtainable from technical-grade aliphatic alcohol cuts and technical-grade, aliphatic carboxylic acid mixtures, e.g. esters of unsaturated fatty alcohols, having 12 to 22 carbon atoms and saturated and unsaturated fatty acids having 12 to 22 carbon atoms, as are accessible from animal and vegetable fats. Also suitable, however, are naturally occurring monoester and/or wax ester mixtures, as are present, for example in jojoba oil or in sperm oil. Suitable dicarboxylic acid esters are, for example, di-n-butyl adipate, di-n-butyl sebacate, di(2-ethylhexyl) adipate, di(2-hexyldecyl) succinate, diisotridecyl azelate. Suitable diol esters are, for example, ethylene glycol dioleate, ethylene glycol diisotridecanoate, propylene glycol di(2-ethylhexanoate), butanediol diisostearate, butanediol dicaprylate/caprate and neopentyl glycol dicaprylate. Further fatty acid esters which can be used as emollients are, for example, $C_{12-15}$ alkyl benzoate, dicaprylyl carbonate, diethylhexyl carbonate. Emollients and oil components which can likewise be used are longer-chain triglycerides, i.e. triple esters of glycerol with three acid molecules, of which at least one is relatively long-chain. By way of example, mention may be made here of fatty acid triglycerides; examples of such which may be used are natural, vegetable oils, e.g. olive oil, sunflower oil, soybean oil, peanut oil, rapeseed oil, almond oil, sesame oil, avocado oil, castor oil, cocoa butter, palm oil, but also the liquid fractions of coconut oil or of palm kernel oil, and also animal oils, such as, for example, shark liver oil, cod liver oil, whale oil, beef tallow and butter fat, waxes such as beeswax, carnauba palm wax, spermaceti, lanolin and neat's-foot oil, the liquid fractions of beef tallow and also synthetic triglycerides of capryl/capric acid mixtures, triglycerides of technical-grade oleic acid, triglycerides with isostearic acid, or from palmitic acid/oleic acid mixtures as emollients and oil components. Furthermore, hydrocarbons, in particular also liquid paraffins and isoparaffins, can be used. Examples of hydrocarbons which can be used are paraffin oil, isohexadecane, polydecene, vaseline, Paraffinum perliquidum, squalane, ceresin. Furthermore, it is also possible to use linear or branched fatty alcohols such as oleyl alcohol or octyldodecanol, and also fatty alcohol ethers such as dicaprylyl ether. Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes. Suitable further oil bodies are, for example, Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched $C_8$-$C_{18}$-alcohols, in particular 2-ethylhexanol or isononanol, esters of branched $C_6$-$C_{13}$-carboxylic acids with branched alcohols, in particular 2-ethylhexanol or isononanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, vegetable oils, branched primary alcohols, substituted cyclohexanes, linear $C_6$-$C_{22}$-fatty alcohol carbonates, Guerbet carbonates, esters of benzoic acid with linear and/or branched $C_6$-$C_{22}$-alcohols (e.g. Finsolv™ TN), dialkyl ethers, ring-opening products of epoxidized fatty acid esters with polyols, silicone oils and/or aliphatic or naphthenic hydrocarbons.

Emulsifiers or surfactants which may be used are nonionic, anionic, cationic or amphoteric surfactants.

Nonionogenic emulsifiers or surfactants which can be used are compounds from at least one of the following groups:

addition products of from 2 to 100 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12/18}$-fatty acid mono- and diesters of addition products of from 1 to 100 mol of ethylene oxide onto glycerol, glycerol mono- and diesters and sorbitan mono- and diesters of saturated and unsaturated fatty acids having 6 to 22 carbon atoms and ethylene oxide addition products thereof, alkyl mono- and oligoglycosides having 8 to 22 carbon atoms in the alkyl radical and ethylene oxide addition products thereof, addition products of from 2 to 200 mol of ethylene oxide onto castor oil and/or hydrogenated castor oil, partial esters based on linear, branched, unsaturated or saturated $C_6$-$C_{22}$-fatty acids, ricinoleic acid, and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), mono-, di- and trialkylphosphates, and mono-, di- and/or tri-PEG alkyl phosphates and salts thereof, polysiloxane-polyether copolymers (dimethicone copolyols), such as, for example PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 4/12 or 20/20 or 18/18 or 17/18 or 15/15, polysiloxane-polyalkyl-polyether copolymers and corresponding derivatives, such as, for example, lauryl or cetyl dimethicone copolyols, in particular cetyl PEG/PPG-10/1 dimethicone (ABIL® EM 90 (Evonik)), mixed esters of pentaerythritol, fatty acids, citric acid and fatty alcohol as in DE 11 65 574 and/or mixed esters of fatty acids having 6 to 22 carbon atoms, methylglucose and polyols, such as, for example, glycerol or polyglycerol, citric acid esters, such as, for example, glyceryl stearate citrate, glyceryl oleate citrate and dilauryl citrate.

Anionic emulsifiers or surfactants can contain water-solubilizing anionic groups, such as, for example, a carboxylate, sulphate, sulphonate or phosphate group and a lipophilic radical. Skin-compatible anionic surfactants are known to the person skilled in the art in large numbers and are commercially available. Here, these may be alkyl sulphates or alkyl phosphates in the form of their alkali metal, ammonium or alkanolammonium salts, alkyl ether sulphates, alkyl ether carboxylates, acyl sarcosinates, and sulphosuccinates and acyl glutamates in the form of their alkali metal or ammonium salts.

Cationic emulsifiers and surfactants can also be added.

Those which can be used are, in particular, quaternary ammonium compounds, in particular those provided with at least one linear and/or branched, saturated or unsaturated alkyl chain having 8 to 22 carbon atoms, such as, for example, alkyltrimethylammonium halides, such as, for example, cetyltrimethylammonium chloride or bromide or behenyltrimethylammonium chloride, but also dialkyldimethylammonium halides, such as, for example, distearyldimethylammonium chloride.

Furthermore, monoalkylamidoquats such as, for example, palmitamidopropyltrimethylammonium chloride or corresponding dialkylamidoquats, can be used.

Furthermore, readily biodegradable quaternary ester compounds can be used; these may be quaternized fatty acid esters based on mono-, di- or triethanolamine. Furthermore, alkylguanidinium salts can be added as cationic emulsifiers.

Typical examples of mild, i.e. particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, the latter for example based on wheat proteins.

Furthermore, it is possible to use amphoteric surfactants, such as, for example, betaines, amphoacetates or amphopropionates, thus, for example, substances such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacylaminoethyl hydroxyethylcarboxymethyl glycinate.

Of the ampholytic surfactants, it is possible to use those surface-active compounds which, apart from a C8/18-alkyl or -acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Further examples of ampholytic surfactants are N-cocoalkylaminopropionate, cocoacylaminoethylaminopropionate and C12/18-acylsarcosine.

Suitable thickeners are, for example, polysaccharides, in particular xanthan gum, guar-guar, agar agar, alginates and tyloses, carboxymethylcellulose and hydroxyethylcellulose, also relatively high molecular weight polyethylene glycol mono- and diesters of fatty acids, polyacrylates (e.g. Carbopols™ or Synthalens™), polyacrylamides, polyvinyl alcohol and polyvinylpyrrolidone, surfactants such as, for example, ethoxylated fatty acid glycerides, esters of fatty acids with polyols, such as, for example, pentaerythritol or trimethylolpropane, fatty alcohol ethoxylates with a narrowed homologue distribution or alkyl oligoglucosides, and also electrolytes such as sodium chloride and ammonium chloride.

Suitable thickeners for thickening oil phases are all thickeners known to the person skilled in the art. In particular, mention is to be made here of waxes, such as hydrogenated castor wax, beeswax or microwax. Furthermore, inorganic thickeners can also be used, such as silica, alumina or sheet silicates (e.g. hectorite, laponite, saponite). In this connection, these inorganic oil phase thickeners may be hydrophobically modified. For the thickening/stabilization of water-in-oil emulsions, in particular aerosils, sheet silicates and/or metal salts of fatty acids, such as, for example, zinc stearate, can be used here.

Viscosity regulators for aqueous surfactant systems which may be present are, for example NaCl, low molecular weight non-ionic surfactants, such as cocoamide DEA/MEA and laureth-3, or polymeric, high molecular weight, associative, highly ethoxylated fat derivatives, such as PEG-200 hydrogenated glyceryl palmate.

UV photoprotective filters which can be used are, for example, organic substances which are able to absorb ultraviolet rays and which give off the absorbed energy again in the form of longer-wave radiation, e.g. heat. UVB filters may be oil-soluble or water-soluble. Examples of oil-soluble UVB photoprotective filters are:

3-benzylidenecamphor and derivatives thereof, e.g. 3-(4-methylbenzylidene)camphor, 4-aminobenzoic acid derivatives, such as, for example, 2-ethylhexyl 4-(dimethylamino)benzoate and amyl 4-(dimethylamino)benzoate, esters of cinnamic acid, such as 2-ethylhexyl 4-methoxycinnamate, isopentyl 4-methoxycinnamate, 2-ethylhexyl 2-cyano-3-phenylcinnamate (octocrylene), esters of salicylic acid, such as, for example, 2-ethylhexyl salicylate, 4-isopropylbenzyl salicylate, homomethyl salicylate, derivatives of benzophenone, such as, for example, 2-hydroxy-4-methoxybenzophenone, 2-hydroxy-4-methoxy- 4'-methylbenzophenone, 2,2'-dihydroxy-4-methoxybenzophenone, esters of benzalmalonic acid, such as, for example, di-2-ethylhexyl 4-methoxybenzmalonate, triazine derivatives, such as, for example, 2,4,6-trianilino-(p-carbo-2'-ethyl-1'-hexyloxy)-1,3,5-triazine and octyltriazone, propane-1,3-diones, such as, for example, 1-(4-tert-butylphenyl)-3-(4'-methoxyphenyl)propane-1,3-dione.

Suitable water-soluble UVB photoprotective filters are:

2-phenylbenzimidazole-5-sulphonic acid and the alkali metal, alkaline earth metal, ammonium, alkylammonium, alkanolammonium and glucammonium salts thereof, sulphonic acid derivatives of benzophenone, such as, for example, 2-hydroxy-4-methoxybenzophenone-5-sulphonic acid and its salts, sulphonic acid derivatives of 3-benzylidenecamphor, such as, for example, 4-(2-oxo-3-bornylidene-methyl)benzenesulphonic acid and 2-methyl-5-(2-oxo-3-bornylidene)sulphonic acid and salts thereof.

Suitable typical UVA photoprotective filters are in particular derivatives of benzoylmethane, such as, for example, 1-(4'-tert-butylphenyl)-3-(4'-methoxy-phenyl)propane-1,3-dione or 1-phenyl-3-(4'-isopropyl-phenyl)propane-1,3-dione. The UV-A and UV-B filters can of course also be used in mixtures.

Besides the specified soluble substances, insoluble pigments, namely finely disperse metal oxides or salts are also suitable for this purpose, such as, for example, titanium dioxide, zinc oxide, iron oxide, aluminium oxide, cerium oxide, zirconium oxide, silicates (talc), barium sulphate and zinc stearate. The particles here should have an average diameter of less than 100 nm, e.g. between 5 and 50 nm and in particular between 15 and 30 nm. They can have a spherical shape, although it is also possible to use those particles which have an ellipsoidal shape or a shape which deviates in some other way from the spherical form. A relatively new class of photoprotective filters are micronized organic pigments, such as, for example, 2,2'-methylenebis{6-(2H-benzotriazol-2-yl)-4-(1,1,3,3-tetra-methylbutyl)phenol} with a particle size of <200 nm, which is obtainable, for example, as 50% strength aqueous dispersion.

Further suitable UV photoprotective filters can be found in the overview by P. Finkel in SÖFW-Journal 122, 543 (1996). Besides the two aforementioned groups of primary UV photoprotective filters, it is also possible to use secondary photoprotective agents of the antioxidant type which interrupt the photochemical reaction chain which is triggered when UV radiation penetrates into the skin. Antioxidants which can be used are, for example, superoxide-dismutase, tocopherols (vitamin E), dibutyl-hydroxytoluene and ascorbic acid (vitamin C).

Hydrotropes which can be used for improving the flow behaviour and the application properties are, for example, ethanol, isopropyl alcohol or polyols. Polyols which are suitable here can have 2 to 15 carbon atoms and at least 2 hydroxyl groups.

Typical examples are:

glycerol alkylene glycols, such as, for example, ethylene glycol, diethylene glycol, propylene glycol, butylene glycol, hexylene glycol, and polyethylene glycols with an average molecular weight of from 100 to 1000 daltons, technical-grade oligoglycerol mixtures with a degree of self-condensation of from 1.5 to 10, such as, for example, technical-grade diglycerol mixtures with a diglycerol content of from 40 to 50% by weight, methylol compounds, such as in particular trimethylolethane, trimethylolpropane, trimethylolbutane, pentaerythritol and dipentaerythritol, lower alkyl glucosides, in particular those with 1 to 4 carbon atoms in the alkyl radical, such as, for example, methyl and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine.

Solids which can be used are, for example, iron oxide pigments, titanium dioxide or zinc oxide particles and those additionally specified under "UV protectants". Furthermore, it is also possible to use particles which lead to special sensory effects, such as, for example, nylon-12, boron nitride, polymer particles such as, for example, polyacrylate or polymethyl acrylate particles or silicone elastomers. Fillers which can be used include starch and starch derivatives, such as tapioca starch, distarch phosphate, aluminium starch or sodium starch, octenyl succinate, and pigments which have neither primarily a UV filter effect nor a colouring effect, for example Aerosils® (CAS No. 7631-86-9).

Examples of film formers which can be used, for example, for improving the water resistance are: polyurethanes, dimethicones, copolyol, polyacrylates or PVP/VA copolymer (PVP=polyvinylpyrrolidone, VA=vinyl acetate). Fat-soluble film formers which can be used are: e.g. polymers based on polyvinylpyrrolidone (PVP), copolymers of polyvinylpyrrolidone, PVP/hexadecene copolymer or the PVP/eicosene copolymer.

Pearlescence additives which can be used are, for example, glycol distearates or PEG-3 distearate.

Suitable deodorant active ingredients are, for example, odour concealers such as the customary perfume constituents, odour absorbers, for example the sheet silicates described in the patent laid-open specification DE 40 09 347, of these, in particular montmorillonite, kaolinite, illite, beidelite, nontronite, saponite, hectorite, bentonite, smectite, or also, for example, zinc salts of ricinoleic acid. Antimicrobial agents are likewise suitable for being incorporated. Antimicrobial substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbonilide, quaternary ammonium compounds, clove oil, mint oil, thyme oil, triethyl citrate, farnesol (3,7,11-trimethyl-2,6,10-dodecatrien-1-ol), ethylhexyl glyceryl ether, polyglyceryl-3 caprylate (TEGO® Cosmo P813, Evonik), and the effective agents described in the patent laid-open specifications DE 198 55 934, DE 37 40 186, DE 39 38 140, DE 42 04 321, DE 42 29 707, DE 42 29 737, DE 42 38 081, DE 43 09 372, DE 43 24 219 and EP 666 732.

Antiperspirant active ingredients which may be used are astringents, for example basic aluminium chlorides such as aluminium chlorohydrate ("ACH") and aluminium zirconium glycine salts ("ZAG").

Insect repellents which may be used are, for example, N,N-diethyl-m-toluamide, 1,2-pentanediol or Insect Repellent 3535.

Self-tanning agents which can be used are, for example, dihydroxyacetone and erythrulose.

Preservatives which can be used are, for example, mixtures of one or more alkyl paraben esters with phenoxyethanol. The alkyl paraben esters may be methyl paraben, ethyl paraben, propyl paraben and/or butyl paraben. Instead of phenoxyethanol, it is also possible to use other alcohols, such as, for example, benzyl alcohol or ethanol. Moreover, it is also possible to use other customary preservatives such as, for example, sorbic acid or benzoic acid, salicylic acid, 2-bromo-2-nitropropane-1,3-diol, chloroacetamide, diazolidinylurea, DMDM hydantoin, iodopropynyl butylcarbamate, sodium hydroxymethylglycinates, methylisothiazoline, chloromethylisothiazoline, ethylhexylglycerol or caprylyl glycol.

Conditioning agents which can be used are, for example, organic quaternary compounds, such as cetrimonium chloride, dicetyldimonium chloride, behentrimonium chloride, distearyldimonium chloride, behentrimonium methosulphate, distearoylethyldimonium chloride, palmitamidopropyltrimonium chloride, guar hydroxypropyltrimonium chloride, hydroxypropylguar, hydroxypropyltrimonium chloride, or quaternium-80 or else amine derivatives such as, for example, aminopropyldimethicones or stearamidopropyldimethylamines.

Perfumes which can be used are natural or synthetic odorants or mixtures thereof. Natural odorants are extracts from flowers (lily, lavender, rose, jasmine, neroli, ylang-ylang), stems and leaves (geranium, patchouli, petitgrain), fruits (anise, coriander, caraway, juniper), fruit peels (bergamot, lemon, orange), roots, (maize, angelica, celery, cardamon, costus, iris, thyme), needles and branches (spruce, fir, pine, dwarf-pine), resins and balsams (galbanum, elemi, benzoin, myrrh, olibanum, opoponax). Animal raw materials are also suitable, such as, for example, civet and castoreum. Typical synthetic odorant compounds are products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include primarily the terpenes and balsams. It is possible to use mixtures of different odorants which together produce a pleasant scent note. Essential oils of low volatility, which are mostly used as aroma components, are also suitable as perfumes, e.g. sage oil, camomile oil, clove oil, Melissa oil, mint oil, cinnamon leaf oil, linden blossom oil, juniperberry oil, vetiver oil, olibanum oil, galbanum oil, labolanum oil and lavandin oil. It is also possible to use bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, Evernyl, Iraldein gamma, phenylacetic acid, geranyl acetate, benzyl acetate, rose oxide, romillat, irotyl and floramat alone or in mixtures.

Dyes which can be used are the substances approved and suitable for cosmetic purposes, as are listed, for example, in the publication "Cosmetic Colorants" of the Dyes Commission of the German Research Society, Verlag Chemie, Weinheim, 1984, pp. 81 to 106. These dyes are usually used in concentrations of from 0.001 to 0.1% by weight, based on the total mixture.

Cosmetic active ingredients are to be understood as meaning, for example, tocopherol, tocopherol acetate, tocopherol palmitate, ascorbic acid, deoxyribonucleic acid, coenzyme Q10, retinol, bisabolol, allantoin, panthenol, phytantriol, AHA acids, amino acids, hyaluronic acid, alpha-hydroxy acids, polyglutamic acid, creatine (and creatine derivatives), guanidine (and guanidine derivatives), ceramides, phytosphingosine (and phytosphingosine derivatives), sphingosine (and sphingosine derivatives), pseudoceramides, sphingolipids, essential oils, peptides and oligopeptides, protein hydrolysates, plant extracts and vitamin complexes.

Care additives which may be present are, for example, ethoxylated glycerol fatty acid esters, such as, for example, PEG-7 glycerol cocoate, or cationic polymers, such as, for example, polyquaternium-7 or polyglycerol esters.

Superfatting agents which can be used are substances such as, for example, lanolin and lecithin, and also polyethoxylated or acylated lanolin and lecithin derivatives, polyol fatty acid esters, monoglycerides and fatty acid alkanolamides, with the latter simultaneously serving as foam stabilizers.

Solvents which can be used are, for example, aliphatic alcohols such as ethanol, propanol or 1,3-propanediol, cyclic carbonates, such as ethylene carbonate, propylene carbonate, glycerol carbonate, esters of mono- or polycarboxylic acids such as ethyl acetate, ethyl lactate, dimethyl adipate and diethyl adipate, propylene glycol, dipropylene glycol, glycerol, glycerol carbonate or water.

In a preferred embodiment, the cosmetic, dermatological or pharmaceutical formulations according to the invention and also the care and cleaning compositions comprise, as additional component, pigments (e.g. $TiO_2$, $FeO_x$ ZnO, mica and, for example, those listed under UV filter substances and solids) or particles (e.g. silicone elastomers, nylon-12, PMMA, boron nitride and, for example, those listed under UV filter substances and solids).

In a likewise preferred embodiment, the cosmetic, dermatological or pharmaceutical formulations according to the invention and also the care and cleaning compositions comprise cosmetic active ingredients as additional component.

The use of emulsifier systems according to the invention or of the emulsion or dispersion according to the invention for the preparation of cosmetic or pharmaceutical formulations is preferred.

The emulsifier systems according to the invention can either be used in the form of O/W emulsifiers or else in the form of W/O emulsifiers, depending on their hydrophilicity.

The application forms of the emulsions and dispersions comprising the emulsifier system according to the invention are therefore sprays, lotions, creams, ointments, and thus use over a very broad consistency range from water-thin to very pasty, in the extreme case even solid, is possible.

Consequently, the emulsifier systems can be used, for example, in care creams and lotions for face, body and hands, in sunscreen emulsions, in make-up, in aerosols, roll-ons, pump sprays, sticks, e.g. in the anti-perspirant/deodorant sector, in baby care products, in intimate care products, foot care products, haircare products, nail care products, dental care products or mouth care products and also in dermatological ointments.

The present invention is described by way of example in the examples listed below, without any intention to limit the invention, the scope of application of which arises from the entire description and the claims, to the embodiments specified in the examples.

EXAMPLES

Emulsifier Examples

Emulsifier 1 (According to the Invention) (O/W Emulsifier)

Preparation: firstly, 183 g of an SiH-functional siloxane of the general formula $Me_3SiO(SiMe_2O)_{28}(SiMeHO)_{10}SiMe_3$ were mixed with 143 g of a vinylsiloxane of the general formula $CH_2=CH-SiMe_2O-(SiMe_2O)_{348}-SiMe_2-CH=CH_2$, heated to 120° C. and treated with 1 ppm of an Rh catalyst. After 30 min, 1322 g of an allyl polyether of the general formula $CH_2=CH-CH_2-O-(CH_2CH_2O)_{25}(CH_2CH(CH_3)O)_4Me$ were then added, the mixture was left to cool to 94° C. and 8 ppm of a platinum catalyst were added. The mixture was then further stirred for 2 h at 120° C.

Emulsifier 2 (According to the Invention) (O/W Emulsifier)

Preparation: firstly, 42 g of an SiH-functional siloxane of the general formula $Me_3SiO(SiMe_2O)_{38}-(SiMeHO)_9SiMe_3$ were mixed with 21 g of a vinylsiloxane of the general formula $CH_2=CH-SiMe_2O-(SiMe_2O)_{280}-SiMe_2-CH=CH_2$, heated to 120° C. and treated with 1 ppm of an Rh catalyst. After 30 min, 148 g of an allyl polyether of the general formula $CH_2=CH-CH_2-O-(CH_2CH_2O)_{25}(CH_2CH(CH_3)O)_4Me$ were then added, the mixture was left to cool to 90° C. and 10 ppm of a Pt catalyst were added. The mixture was then further stirred for 2 h at 120° C. and the product was filtered.

Emulsifier 3 (According to the Invention) (W/O Emulsifier)

Preparation: firstly, 144 g of an SiH-functional siloxane of the general formula $Me_3SiO(SiMe_2O)_{73}(SiMeHO)_{25}SiMe_3$ were mixed with 26 g of a vinylsiloxane of the general formula $CH_2=CH-SiMe_2O-(SiMe_2O)_{348}-SiMe_2-CH=CH_2$, heated to 90° C. and treated with 5 ppm of a platinum catalyst. Subsequently, 32 g of an allyl polyether of the general formula $CH_2=CH-CH_2-O-(CH_2CH_2O)_8OH$ and 117 g of 1-hexadecene were then added. During this, the temperature increased to 113° C. The mixture was then stirred for a further 2 h at 110° C. and the product was freed from volatile constituents in vacuo.

Comparative Examples 1-6 (not According to the Invention, for Distinguishing from the Prior Art)

The structure of the comparative emulsifiers 1 to 5 corresponds to the general formula:

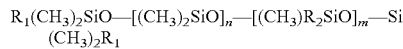

where: $R_1$, $R_2$=$CH_3$ or a polyether ("PE") of the type: $-(CH_2)_w-O-(C_2H_4O)_x-(C_3H_6O)_y-R_3$ where $R_3$=H or $CH_3$

| Comparative Emulsifier | n | m | $R_1$ | $R_2$ | $R_3$ | w | x | y |
|---|---|---|---|---|---|---|---|---|
| 1 | 66 | 0 | PE | — | H | 3 | 13 | 0 |
| 2 | 50 | 0 | PE | — | $CH_3$ | 3 | 15 | 10 |
| 3 | 200 | 0 | PE | — | H | 3 | 13 | 20 |
| 4 | 100 | 0 | PE | — | H | 3 | 11 | 17 |
| 5 | 45 | 5 | $CH_3$ | PE | H | 3 | 20 | 20 |

The comparative emulsifiers 1-4 correspond to Examples 1-4 of EP 1125574.

Comparative emulsifier 5 is a typical silicone polyether with a comb-like structure.

A further comparative emulsifier 6 differs from emulsifiers according to the invention by virtue of the very short siloxane chain length of the bridging siloxane which when d=0 lies outside of the scope claimed by this invention.

Preparation of Comparative Emulsifier 6 (not According to the Invention) (O/W Emulsifier)

Firstly, 240 g of an SiH-functional siloxane of the general formula $Me_3SiO(SiMe_2O)_{28}(SiMeHO)_{10}SiMe_3$ were mixed with 1.3 g of a vinylsiloxane of the general formula $CH_2=CH-SiMe_2O-SiMe_2-CH=CH_2$, heated to 120° C. and the mixture was treated with 1 ppm of an Rh catalyst. After 30 min, 1732 g of an allyl polyether of the general formula $CH_2=CH-CH_2-O-(CH_2CH_2O)_{25}(CH_2CH(CH_3)O)_4Me$ were then added, the mixture was left to cool to 94° C. and 8 ppm of a platinum catalyst were added. The mixture was then stirred for a further 2 h at 120° C.

Application Examples

All of the concentrations given in the application examples are in percentages by weight. To prepare the emulsions customary homogenization processes known to the person skilled in the art were used.

Emulsifying Power

To investigate the emulsifying power in O/W emulsions, a rapid test was used which very rapidly shows under very critical conditions (only 0.5% emulsifier) which structures are distinguished by excellent emulsifying activity.

Using customary oils and stabilizers, the stability after storage for 24 h at 50° C. in particular shows very clearly whether an emulsifier has very good stabilizing properties.

The results of emulsifiers 1 and 2 according to the invention compared to the results of the comparative emulsifiers 1 to 5 are summarized in Table 1.

The preparation of the emulsions was carried out here in accordance with the following process:

Phases A and B are mixed at room temperature, phase C is added without stirring. The mixture is then homogenized for 1 min. Phases D and E are added, then homogenized again for 1 min.

The results of emulsion examples 1 and 2 show that the emulsifiers according to the invention have considerably higher stabilization properties than the comparative emulsifiers 1-4 (α-ω modified siloxanes from EP 1125574) or comparative emulsifier 5 (typical comb-like modified polyethersiloxane).

TABLE 1

Composition and evaluation of the investigations in the emulsion rapid test.

| | Examples | 1 | 2 | C1 | C2 | C3 | C4 | C5 |
|---|---|---|---|---|---|---|---|---|
| A | Emulsifier 1 | 0.5% | | | | | | |
| | Emulsifier 2 | | 0.5% | | | | | |
| | Comparative Emulsifier 1 | | | 0.5% | | | | |
| | Comparative Emulsifier 2 | | | | 0.5% | | | |
| | Comparative Emulsifier 3 | | | | | 0.5% | | |
| | Comparative Emulsifier 4 | | | | | | 0.5% | |
| | Comparative Emulsifier 5 | | | | | | | 0.5% |
| | Ethylhexyl stearate | 9.0% | 9.0% | 9.0% | 9.0% | 9.0% | 9.0% | 9.0% |
| | Paraffinum perliquidum | 9.0% | 9.0% | 9.0% | 9.0% | 9.0% | 9.0% | 9.0% |
| | Ethanol | 5.0% | 5.0% | 5.0% | 5.0% | 5.0% | 5.0% | 5.0% |
| B | Carbomer | 0.16% | 0.16% | 0.16% | 0.16% | 0.16% | 0.16% | 0.16% |
| | Ethylhexyl stearate | 1.04% | 1.04% | 1.04% | 1.04% | 1.04% | 1.04% | 1.04% |
| C | Demineralized water | ad 100% | ad 100% | ad 100% | ad 100% | ad 100% | ad 100% | ad 100% |
| D | NaOH (5% solution) | 1.25% | 1.25% | 1.25% | 1.25% | 1.25% | 1.25% | 1.25% |
| E | Euxyl ® K 300[1] | 0.70% | 0.70% | 0.70% | 0.70% | 0.70% | 0.70% | 0.70% |
| | Stability after 24 h at 50° C. | stable | stable | Oil separation severe coalescence | Oil separation severe coalescence | Oil separation severe coalescence | Oil separation severe coalescence | Oil separation severe coalescence |

[1] Euxyl ® K 300 (Schülke & Mayr): Phenoxyethanol, Methylparaben, Ethylparaben, Propylparaben, Butylparaben, Isopropylparaben Skin Feel and Emulsion Stability:

In order to investigate skin feel and stability of the two emulsifier examples 1 and 2 according to the invention, these were used in a concentration of 2% in a cosmetic formulation (emulsion examples 3 and 4).

The comparative examples used were the comparative emulsifiers 1, 2, 4, 5 and 6 (comparative emulsion examples C6-C10).

The skin feel of the corresponding emulsion was evaluated in a panel of 10 subjects compared in each case to the formulation containing comparative emulsifier 1.

The test results are summarized in Table 2.

In these example formulations, it becomes clear that only with the emulsifiers according to the invention is it possible to prepare formulations which are both stable and also advantageous from the point of view of skin feel.

In particular, C10 shows that although a bridged siloxane outside of the scope of claim 1 leads to a relatively good emulsion stability, the skin feel of the formulation is significantly behind the examples according to the invention.

TABLE 2

Skin feel and stability data of test emulsions

| Examples | 3 | 4 | C6 | C7 | C8 | C9 | C10 |
|---|---|---|---|---|---|---|---|
| Emulsifier 1 | 2.00% | | | | | | |
| Emulsifier 2 | | 2.00% | | | | | |
| Comparative Emulsifier 1 | | | 2.00% | | | | |
| Comparative Emulsifier 2 | | | | 2.00% | | | |
| Comparative Emulsifier 4 | | | | | 2.00% | | |
| Comparative Emulsifier 5 | | | | | | 2.00% | |
| Comparative Emulsifier 6 | | | | | | | 2.00% |
| Ethylhexyl stearate | 10.0% | 10.0% | 10.0% | 10.0% | 10.0% | 10.0% | 10.0% |
| Paraffinum perliquidum | 9.0% | 9.0% | 9.0% | 9.0% | 9.0% | 9.0% | 9.0% |
| Carbomer | 0.16% | 0.16% | 0.16% | 0.16% | 0.16% | 0.16% | 0.16% |
| Xanthan gum | 0.16% | 0.16% | 0.16% | 0.16% | 0.16% | 0.16% | 0.16% |
| Demineralized water | ad 100% | ad 100% | ad 100% | ad 100% | ad 100% | ad 100% | ad 100% |
| NaOH (5% solution) | 1.25% | 1.25% | 1.25% | 1.25% | 1.25% | 1.25% | 1.25% |
| Euxyl ® K 300[1] | 0.70% | 0.70% | 0.70% | 0.70% | 0.70% | 0.70% | 0.70% |
| Stability | stable | stable | oil separation | oil separation | oil separation | severe | slight |

TABLE 2-continued

Skin feel and stability data of test emulsions

| Examples | 3 | 4 | C6 | C7 | C8 | C9 | C10 |
|---|---|---|---|---|---|---|---|
| after 3 months | | | severe coalescence | severe coalescence | severe coalescence | coalescence | coalescence |
| Skin feel | soft, smooth, velvety | soft, smooth, velvety | soft, smooth, velvety | soft, smooth, somewhat oily | soft, smooth, velvety | dry, somewhat sticky | dry, sticky |

Further Emulsion Examples

These examples are intended to show that the emulsifiers according to the invention can be used in a large number of cosmetic formulations. It is possible to prepare O/W or W/O emulsions depending on the hydrophilicity of the emulsifiers according to the invention. Moreover, it is possible with the aid of the emulsifiers according to the invention to stably incorporate pigments or solids into emulsion preparations. Furthermore, the examples exhibit the good compatibility with typical coemulsifiers, oils, thickeners, and stabilizers.

O/W Emulsion Examples

Anti-Ageing Day Cream

| Example | 5 |
|---|---|
| Emulsifier 1 | 1.50% |
| Ceteareth-25 | 1.00% |
| Stearyl alcohol | 1.50% |
| Glyceryl stearate | 3.00% |
| Stearic acid | 1.50% |
| Myristyl myristate | 1.00% |
| Ceramide IIIB | 0.10% |
| Caprylic/capric triglyceride | 5.00% |
| Ethylhexyl palmitate | 4.40% |
| Ethylhexyl methoxycinnamate | 2.00% |
| Butyl methoxydibenzoyl-methane | 1.00% |
| Glycerol | 3.00% |
| Water | ad 100% |
| TEGO ® Carbomer 134 (Carbomer) | 0.10% |
| Ethylhexyl palmitate | 0.40% |
| Sodium hydroxide (10% in water) | q.s. |
| Preservative | q.s. |
| Perfume | q.s. |

Self-Tanning Body Lotion:

| Example | 6 |
|---|---|
| Emulsifier 2 | 1.00% |
| ABIL ® Care 85 (bis-PEG/PPG-16/16 PEG/PPG-16/16 dimethicone; caprylic/capric triglyceride) | 1.00% |
| Cetearyl isononanoate | 5.00% |
| Decyl cocoate | 5.00% |
| Isopropyl myristate | 5.00% |
| Sepigel ® 305 (polyacrylamide; C13-14 isoparaffin; laureth-7) | 1.50% |
| PEG-30 glyceryl stearate | 2.00% |
| Dihydroxyacetone | 5.00% |
| Propylene glycol | 3.00% |
| Water | ad 100% |

-continued

| Example | 6 |
|---|---|
| Citric acid | q.s. |
| Preservative | q.s. |
| Perfume | q.s. |

Cationic Sunscreen Cream (In Vitro SPF 18):

| Example | 7 |
|---|---|
| Emulsifier 1 | 2.00% |
| Distearyldimonium chloride | 1.50% |
| Glyceryl stearate | 2.00% |
| Stearyl alcohol | 1.00% |
| C12-15 alkyl benzoate | 5.00% |
| TEGO ® Sun TDEC 45 (titanium dioxide; diethylhexyl carbonate; polyglyceryl-6 polyhydroxystearate) | 5.00% |
| Diethylhexyl carbonate | 3.50% |
| Cetyl ricinoleate | 1.00% |
| Triisostearin | 1.00% |
| Octocrylene | 3.00% |
| Ethylhexyl methoxycinnamate | 4.00% |
| Butyl methoxydibenzoyl-methane | 2.00% |
| Water | ad 100% |
| Glycerol | 3.00% |
| Preservative | q.s. |
| Perfume | q.s. |

Skin-Smoothing Body Lotion:

| Example | 8 |
|---|---|
| Emulsifier 1 | 1.00% |
| ABIL ® Care 85 (bis-PEG/PPG-16/16 PEG/PPG-16/16 dimethicone; caprylic/capric triglyceride) | 1.00% |
| Diethylhexyl carbonate | 7.00% |
| Isopropyl palmitate | 7.60% |
| Polysorbate 20 | 0.20% |
| Creatine | 0.50% |
| Panthenol | 0.50% |
| Glycerol | 3.00% |
| Water | ad 100% |
| TEGO ® Carbomer 341 ER (acrylates/C10-30 alkyl acrylate cross-polymer) | 0.30% |
| Xanthan gum | 0.10% |
| Sodium hydroxide (10% in water) | q.s. |
| TEGO ® smooth complex (betaine; urea; potassium lactate; polyglutamic acid; hydrolyzed sclerotium gum) | 2.00% |
| Preservative | q.s. |
| Perfume | q.s. |

Silky Cream Gel:

| Example | 9 |
|---|---|
| Emulsifier 2 | 2.00% |
| Bis-PEG/PPG-14/14 dimethicone | 2.00% |
| Cyclomethicone | 10.00% |
| Dimethicone | 3.00% |
| Cetyl ricinoleate | 2.00% |
| Xanthan gum | 0.20% |
| TEGO ® Carbomer 341 ER (acrylates/C10-30 alkyl acrylate cross-polymer) | 0.40% |
| Caprylic/capric triglyceride | 1.90% |
| Water | ad 100% |
| PEG/PPG-20/20 dimethicone | 1.00% |
| Alcohol | 5.00% |
| Sodium hydroxide (10% in water) | q.s. |
| Preservative | q.s. |
| Perfume | q.s. |

W/O Emulsion Examples

W/Si Lotion

| Example | 10 |
|---|---|
| Emulsifier 3 | 1.50% |
| Cyclopentasiloxane | 19.50% |
| NaCl | 0.50% |
| Glycerol | 3.00% |
| Water | ad 100% |
| Preservative | q.s. |
| Perfume | q.s. |

Water-Resistant Sunscreen:

| Example | 11 |
|---|---|
| Emulsifier 3 | 2.50% |
| C12-15 alkyl benzoate | 10.00% |
| Paraffinum perliquidum | 13.50% |
| Cetyl dimethicone | 1.00% |
| Titanium dioxide | 5.00% |
| Sodium chloride | 0.50% |
| Water | ad 100% |
| Preservative | q.s. |
| Perfume | q.s. |

Make-Up Foundation:

| Example | 12 |
|---|---|
| Emulsifier 3 | 3.00% |
| Diethylhexyl carbonate | 10.00% |
| Cyclopentasiloxane | 12.60% |
| Iron oxides | 1.80% |
| Titanium dioxide | 7.20% |
| Talc | 2.00% |
| Ethylhexyl palmitate | 3.40% |
| NaCl | 1.00% |
| Glycerol | 2.00% |
| Water | ad 100% |
| Preservative | q.s. |
| Perfume | q.s. |

O/W Impregnation Emulsion for Cosmetic Wet Wipes

| Example | | 13 |
|---|---|---|
| A | TEGO ® Wipe DE (diethylhexyl carbonate; polyglyceryl-4 laurate; phenoxyethanol; methyl-paraben; dilauryl citrate; ethylparaben; butyl-paraben; propylparaben; isobutylparaben) | 5.70% |
| B | Demineralized water | 5.70% |
| C | Emulsifier 1 | 0.30% |
|   | Creatine | 0.25% |
|   | Panthenol | 0.50% |
|   | Demineralized water | 93.25 |
| Z | Perfume | q.s. |

Preparation: at room temperature, A is firstly mixed with B, then C and Z are added with stirring.

The invention claimed is:
1. An emulsifier system comprising an organomodified siloxane block copolymer and a co-emulsifier, wherein the organomodified siloxane block copolymer is prepared by:
A) addition reaction of organopolysiloxanes of the general formula I

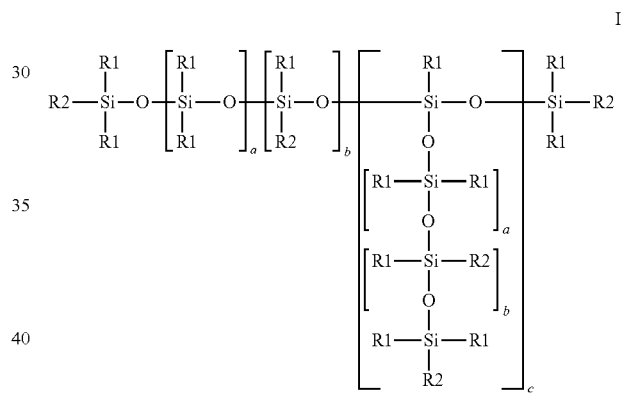

in which
R$^1$ are identical or different aliphatic or aromatic hydrocarbon radicals having 1 to 20 carbon atoms,
R$^2$ is R$^1$ or H, with the proviso that at least three radicals R$^2$ are H,
a is 5 to 500,
b is 1 to 50,
c is 0 to 5,
onto siloxanes of the general formula II containing double bonds

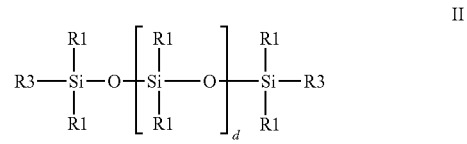

where
d is 10 to 1000 and R$^3$, independently of one another, are identical or different hydrocarbon radicals having 2 to 12 carbon atoms and containing at least one double bond, in the presence of platinum or rhodium catalysts, with the proviso that the organopolysiloxanes of the general formula I are present in at least 6-fold molar excess, based on the siloxane of the general formula II containing double bonds, to give a reaction product having Si—H groups and with further reaction of the reaction product in at least one of the stages B) transition-metal-catalysed partial or complete addition of the SiH groups onto alkenyl and/or alkynyl compounds, or C) partial or complete reaction of the Si—H groups remaining after the above reaction(s) in the presence of a catalyst with at least one alcohol selected from the group consisting of linear or branched, saturated, mono- or polyunsaturated, aromatic, aliphatic-aromatic, optionally halogen-atom-containing monoalcohols, polyether monoalcohols, polyester monoalcohols, and amino alcohols.

2. The emulsifier system according to claim 1, wherein each $R^1$ is an identical or different unbranched, aliphatic or aromatic hydrocarbon radical having 1 to 9 carbon atoms.

3. The emulsifier system according to claim 1, wherein, in step B), the addition is onto polyethers containing double bonds.

4. The emulsifier system according to claim 1, wherein, in step B) the addition is onto allyl polyether.

5. The emulsifier system according to of claim 1, wherein said catalyst in step C) is a boron-containing Lewis acid.

6. The emulsifier system according to claim 5, wherein said boron-containing Lewis acid is tris(pentafluorophenyl)borane $(C_5F_4)_3B$.

7. The emulsifier system according to claim 5, further comprising using in step C) a synergistically effective compound besides said boron-containing Lewis acid.

8. The emulsifier system according to claim 7, wherein said synergistically effective compound is a salt or complexes with cations selected from the group of the salts of elements of the 4th, 6th, 7th and 8th subgroup and of the 4th main group.

9. The emulsifier system according to claim 1, wherein said catalyst of step C) is a catalytic mixture comprising at least one carboxylic acid and at least one salt of a carboxylic acid.

10. The Emulsifier system according to claim 1, wherein the siloxane block copolymer has a viscosity of <10 000 mPas.

11. A dispersion or emulsions comprising the emulsifier system according to claim 1.

12. The dispersion or emulsion according to claim 11, wherein the emulsion is a water-in-oil emulsion, an oil-in-water emulsion or a water-in-silicone emulsion.

13. Cosmetic, dermatological or pharmaceutical formulation comprising the emulsifier system according to claim 1 or at least an emulsion or dispersion comprising said emulsifier system.

14. Cosmetic, dermatological or pharmaceutical formulation according to claim 13 comprising particles or pigments as additional component.

15. Cosmetic, dermatological or pharmaceutical formulation according to claim 13 comprising cosmetic active ingredients as additional component.

16. Care and cleaning composition for domestic use, for hard surfaces, leather or textiles comprising the emulsifier system according to claim 1 or an emulsion or dispersion comprising said emulsifier system.

17. Care and cleaning composition according to claim 16 comprising particles or pigments as additional component.

18. Care and cleaning composition according to claim 16 comprising cosmetic active ingredients as additional component.

* * * * *